United States Patent [19]

Grespin

[11] Patent Number: 4,692,300

[45] Date of Patent: Sep. 8, 1987

[54] DEVICE FOR THE UNDERWATER MEASUREMENT OF THE HARDNESS OF A VERTICAL WALL OF THE PARTITIONING OF THE CORE OF A PRESSURIZED WATER NUCLEAR REACTOR

[75] Inventor: Gerard Grespin, Paris, France

[73] Assignee: Framatome & Cie., Courbevoie, France

[21] Appl. No.: 667,692

[22] Filed: Nov. 2, 1984

[30] Foreign Application Priority Data

Nov. 4, 1983 [FR] France ................ 83 17524

[51] Int. Cl.[4] ............................................ G21C 17/00
[52] U.S. Cl. ........................................ 376/245; 73/78
[58] Field of Search ................ 376/245; 73/781, 786, 73/788, 78, 79

[56] References Cited

U.S. PATENT DOCUMENTS

| | | | |
|---|---|---|---|
| 3,392,086 | 7/1968 | Bret et al. | 376/245 |
| 3,621,580 | 11/1971 | Tovaglieri | 376/245 |
| 3,803,365 | 4/1974 | Cartier | 376/245 |
| 4,421,715 | 12/1983 | Gunter et al. | 376/245 |

Primary Examiner—Salvatore Cangialosi
Attorney, Agent, or Firm—Pollock, Vande Sande & Priddy

[57] ABSTRACT

The invention relates to an underwater measuring device of the hardness of a vertical wall of the partitioning of the core of a pressurized water nuclear reactor. The device comprises a hollow pole for the manipulation from the edge of the pool of the reactor of the pole in vertical position. A body fast to the pole at its lower end contains a first chamber in which is mounted a movable piston bearing support means intended to come into contact with walls at right angles and a second chamber in which is movably mounted a second piston bearing a hardness measuring head designed to form an impression on the wall opposite one of the walls. Hydraulic fluid supply means for the chambers and conductors pass through the hollow pole. The conductors are connected to a measuring station. The invention is applicable particularly to determining the influence of irradiation on the walls of the partitioning of a nuclear reactor, after a certain period of operation.

6 Claims, 2 Drawing Figures

DEVICE FOR THE UNDERWATER MEASUREMENT OF THE HARDNESS OF A VERTICAL WALL OF THE PARTITIONING OF THE CORE OF A PRESSURIZED WATER NUCLEAR REACTOR

FIELD OF THE INVENTION

The invention relates to a device for the underwater measurement of the hardness of a vertical wall of the partitioning of the core of a pressurized water nuclear reactor.

The core of pressurized water nuclear reactors constituted by prismatic assemblies positioned vertically and side by side is generally surrounded by partitioning which permits the cooling water to be channelled in an annular space situated between the partitioning and the core jacket, to bring this cooling water to the base of the core. This partitioning is generally constituted by vertical plates called baffles assembled together to mate strictly the outer shape of the core. The fuel assemblies are generally of square cross-section and assembled so that the outer contour of the core has numerous steps. The vertical plates of the partitioning are hence assembled at a right angle and in view of the symmetry of the core, each of the vertical plates is placed parallel and face to face with another plate of identical dimensions.

The baffles are held by stiffeners or formers positioned in the annular space between the partitioning and the core jacket, whose inner contour reproduces the shape of the cross-section of the core.

During the operation of the reactor, the partitioning is not subject to intense mechanical stresses since the pressure of the cooling water of the reactor is not very different on each side of the partitioning. Only the pressure drop in passing thru the assemblies creates a relatively low pressure difference between the outside and the inside of the partitioning.

However, the partitioning undergoes intense neutron bombardment during the operation of the reactor. Therefrom result structural transformations of the metal constituting the plates of the partitioning.

Even if the materials constituting the partitioning are selected so as only to undergo extremely slow transformations under the effect of the radiation, there are produced in spite of all, transformations resulting in appreciable modifications of the mechanical properties of the partitioning in the course of the operation of the reactor, that is to say over very long periods which can extend up to 40 years.

It may be necessary in the course of the life of the reactor, to introduce certain modifications in the partitioning requiring operations of perforation, tapping or hammering of certain portions of this partitioning. It is then necessary to know with good accuracy the mechanical properties of the plates of the partitioning and their degree of aging.

The hardness measurement can enable a relatively precise idea to be gained on the state of aging of the material and on its other mechanical properties.

In the case of partitioning of a nuclear reactor which has already operated, it is necessary to carry out these operations underwater to ensure sufficient biological protection of the personnel carrying out the checks. The operations must be done from the edge of the pool of the reactor, when the tank of the reactor is open and placed in communication with this pool, during maintenance operations between two periods of operation of the reactor.

Until now no device was known enabling hardness measurements of great accuracy to be carried out on vertical partitions, located underwater and having a certain radioactivity. One of the difficulties arises because the hardness measurement must be effected with a measuring head arranged horizontally to form an impression in the vertical plate on which the hardness measurement is effected.

SUMMARY OF THE INVENTION

It is therefore an object of the invention to provide a device for measuring underwater, the hardness of vertical walls of the partitioning of the core of a pressurized water nuclear reactor comprising vertical partitions arranged in parallel and facing pairs and each assembled at a right angle with other vertical walls of the partitioning, this device enabling rapid and accurate measurement from the edge of the pool of the reactor.

Accordingly, the measuring device according to the invention comprises:

a hollow pole for the manipulation of the device from the edge of the pool of the reactor, the pole being vertical in service position, a body fast to the pole at its lower end having its axis perpendicular to the pole and hence horizontal in service position, a first chamber formed in the horizontal body along its axis and at one of its ends, a first piston mounted axially movable in the first chamber bearing support means intended to come into contact with a first set of two walls arranged at a right angle, a second chamber formed in the horizontal body along its axis and at its end opposite the first chamber, a second piston mounted axially movable in this second chamber bearing a hardness measuring head designed to make an impression on one of the walls opposite the support walls, the horizontal body being intercalated between these opposite walls during the hardness measurement, supply means of hydraulic fluid to each of the chambers of the horizontal body passing axially through the hollow vertical pole, measuring means of the force exerted by the second piston on the hardness measuring head, accurate measuring means of the movement of the measuring head, and conductors passing axially through the vertical pole for transmitting results of measurement to a measuring station located above the pool of the reactor.

BRIEF DESCRIPTION OF THE DRAWINGS

In order to understand the invention more fully, there will now be described, purely by way of non-limiting example, with reference to the accompanying drawings, one embodiment of a hardness-measuring device according to the invention. In the drawings.

DETAILED DESCRIPTION

Figure 1:
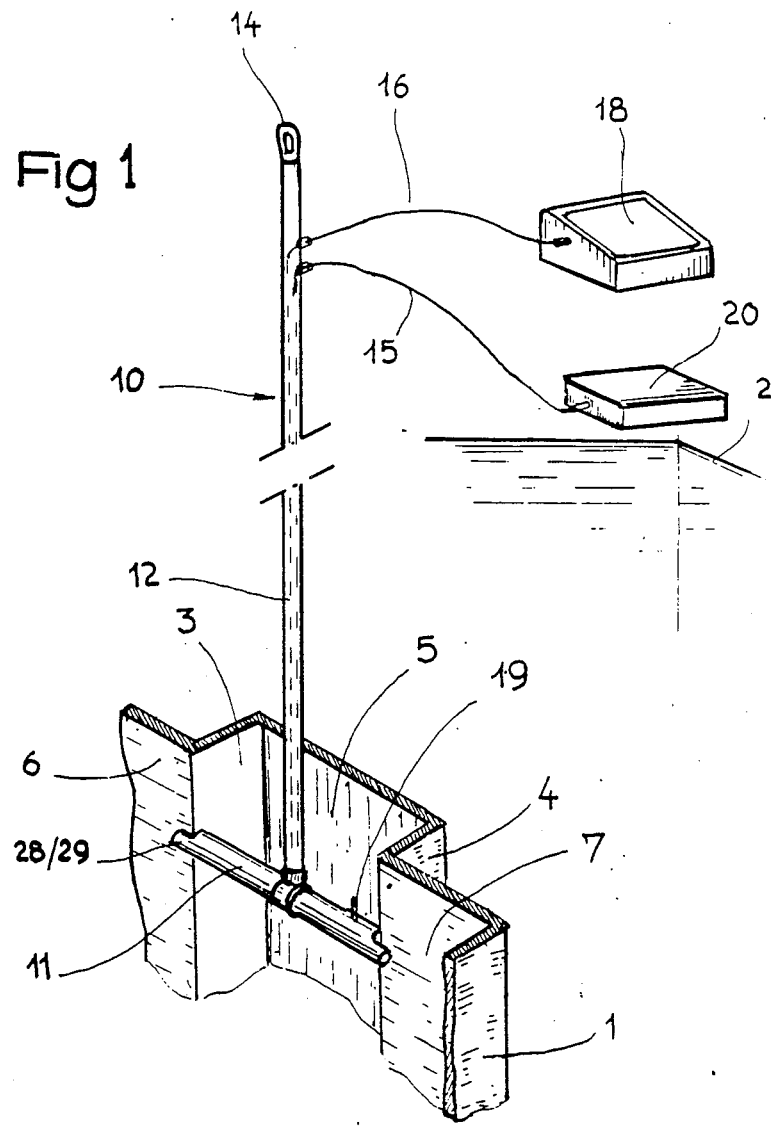
FIG. 1 shows in perspective view, the whole of the hardness-measuring device in service position in the pool of a pressurized water nuclear reactor, during the maintenance of this reactor.

In FIG. 1, is seen a portion of the partitioning 1 of the nuclear reactor arranged inside the tank of the reactor (not shown) and in communication with the pool of the reactor filled with water to a level situated well above the upper portion of the partitioning. The partitioning 1 is constituted in particular by vertical walls or baffles such as 3, 4 and 5.

The walls 3 and 4 are arranged parallel and face to face to constitute the jacket of a step of the outer portion of the core. A wall 5 is assembled at right angles with each of the walls 3 and 4 which are themselves assembled at a right angle with the walls 6 and 7 respectively.

The measuring device 10 has been shown in service position where its lower portion is intercalated between the partitions 3 and 4. This lower portion constituting the body of the measuring device has been shown in detail in FIG. 2.

The device comprises also a very long hollow vertical pole 12 comprising a hooking ring 14 at its upper part for the manipulation of the device by means of a pulley block positioned above the pool 2 of the reactor. The body 11 is fixed to the lower part of the pole 12 so that its axis is perpendicular to this pole which is vertical in its service position.

Inside the hollow pole pass pipes 15 for supplying the body 11 with hydraulic fluid and conductors 16 enabling the collection of the measuring signals necessary to determine the hardness and to transmit them to a measuring station 18 positioned on the edge of the pool of the reactor. A probe 19 enabling radioactivity measurements is also connected to the measuring station 18 through a conductor 16. The hydraulic fluid supply pipes 15 are connected to a circuit 20 enabling supply by a control fluid of the hardness measuring device at a regulated pressure.

Figure 2:
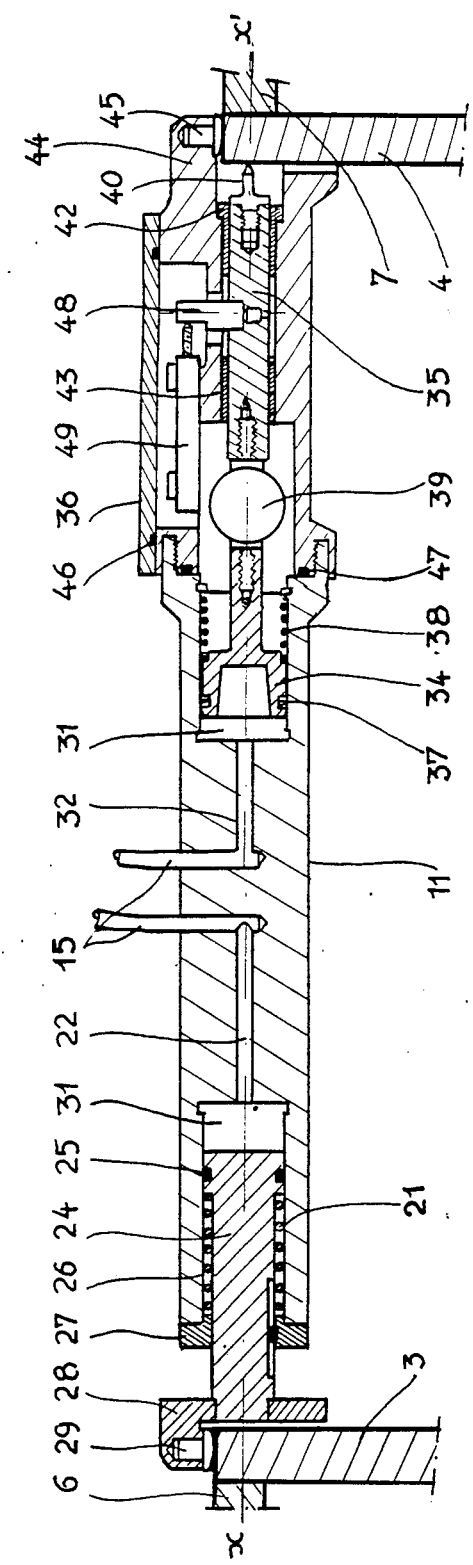
FIG. 2 shows, in a view in cross-section through a horizontal plane, the lower portion of the measuring device, in service position between two walls of the partitioning.

In FIG. 2, is seen the horizontal body 11 of the measuring device intercalated between the wall 3 on which it is supported and the wall 4 on which the hardness measurement is effected.

The body 11 of the device comprises at one of its ends a chamber 21 directed along the horizontal axis xx' of the body 11. This chamber 21 is itself connected to a channel 22 enabling its supply with hydraulic fluid, the channel 22 being placed in communication with one of the fluid supply pipes 15. Inside the chamber 21 is mounted movable in the axial direction, a piston 24 provided with a set of segments 25. When the chamber 21 is not supplied with hydraulic fluid, the piston 24 is held in retracted position in the chamber 21 by means of a spring 26 supported on a closure part of the chamber 27 also ensuring the guidance of the piston 24.

At its end located outside the chamber 21, the piston 24 is connected to a support part 28 of angular shape comprising a stud with a spherical head 29 forming the support of the device on the right-angled edge of the plate 3.

The spherical stud 29 enables support to be taken on the plate 3 even in the case where this plate or the bond with the neighboring plate 6 has a poor bevel.

At its end opposite the chamber 21, the body 11 is machined to form a chamber 31 also of axial direction and opposite the chamber 21. This chamber 31 is connected by a channel 32 to a hydraulic fluid supply pipe 15.

Within the chamber 31 is mounted axially movable a piston 34 bearing the measuring head 35. This measuring head is itself guided and mounted in fluid-tight manner within a positioning and guidance unit 36 fast to the end of the body 11 in which the chamber 31 is formed.

The piston 34 comprises a set of segments 37. A return spring 38 enables the measuring head to be held in retracted position, when the chamber 31 is not supplied with pressurized hydraulic fluid.

The measuring head 35 is connected to the piston 34 through a stress sensor 39 enabling the force exerted by the piston 34 on the measuring head to be measured when the latter is in contact with the wall 4 on which the hardness measurement is carried out. The measuring head 35 comprises at its outer part coming into contact with the wall 4, a diamond tip 40 of pyramidal shape designed to form the hardness impression. This measuring head 35 is mounted axially movable and fluid-tight inside the unit 36, by means of sliding seals 42 and 43.

The positioning and guide means 36 comprises at its front part a support part 44 comprising a spherical stud 45 comparable with the support device 28, 29 positioned at the other end of the horizontal body 11. This support device 44 enables positioning of the measuring head at the angle of the walls 4 and 7, even if a bad bevel of this right angle assembly exists.

The assembly of the device 36 and of the body 11 around the chamber 31, is formed in completely fluid-tight manner by means of seals such as 46 and 47. Generally, the inner part of the positioning device 36 and of the chamber 31 is completely isolated from the water of the pool of the reactor in which the hardness measuring device is immersed. Within this isolated part of the water of the pool of the reactor is found the stress measuring device 39 and an accurate measuring device 49 of the movements of the measuring head. For this measurement, the measuring head 35 is fastened to a lug 48 which remains in contact with the rod of the device 49 formed in the shape of a feeler.

The operation of the device according to the invention will now be described to carry out a hardness measurement of the vertical wall 4 of the partitioning shown in FIG. 1.

The measuring device is hooked to a block and tackle through the ring 14 arranged at the upper part of the rod 12 and lowered into the pool of the reactor so that the horizontal body 11 is placed between the walls 3 and 4. The support part of the device is placed in contact with the wall 3 and the measuring part with the wall 4, in the vicinity of the edges of these walls connected to the walls 6 and 7 respectively. The body 11 of the device is placed in position by an operator placed at the edge of the pool of the reactor having direct view on the partitioning.

Then the chamber 21 is supplied with hydraulic fluid through the pressure-regulated hydraulic circuit 20 and one of the pipes 15. The supply of one or other of the pipes 15 communicating respectively with the channels 22 and 32 is effected by means of electro-valves controlled by the operator.

The outward movement of the piston 24 causes the locking of the part 11 of the measuring device between the parallel facing walls 3 and 4, as shown in FIG. 2.

The pressure in the chamber 21 will be maintained at a fixed value during the whole measurement, the part 36 of the device remaining in contact with the wall 4 on which the hardness measurement is carried out.

Then the second chamber 31 is supplied with hydraulic fluid at a first pressure by means of the corresponding pipe 15 and a slide valve distributor of the hydraulic circuit 20. This first pressure P0 produces a load F0 on the piston 34 and hence on the diamond tip 40 which is driven into the wall 4 by a distance h0, this depth of penetration h0 being measured very accurately by the device 49. In the same way, the load F0 is measured very accurately by the load sensor 39.

The fluid is then introduced into the chamber 31 at a second pressure P1 higher than P0, which causes a load F1>F0 on the piston 34 and on the measuring head 35. The diamond tip is then driven through a height h1>h0 into the wall 4. Then the pressure P0 is reestablished in the chamber 31, so that the force applied to the piston 34 and the measuring head 35 comes back to the value F0. The diamond tip penetrates then by a height h2 into the wall 4. The heights h1, h2 and h0 are such that: h1>h2>h0. The measurement of the values of F1, F0, h1, h2 and h0 enables accurate determination of the Rockwell hardness of the material constituting the plate 4 which has undergone a certain irradiation.

The signals representing the measurements of the loads and of the depths of penetration are transmitted to the measuring station 18 above the pool of the reactor and translated into analog or digital form for exploitation by the operator.

It will be noted that the measuring portion of the device containing the load and displacement sensors is totally isolated from the water of the pool of the reactor by means of fluid-tight seals.

The device can be moved to other walls of which the spacing is equivalent to the spacing of the walls 3 and 4.

It is thus possible to check the hardness and hence the aging and the mechanical properties of the material of the partitioning at various places around the core.

The manipulation of the device is particularly easy and rapid and hardness measurements can be carried out at various heights along the partitioning.

The device according to the invention hence enables very rapid and very easy measurements at fully predetermined places of the partitioning of the core. During all the measuring operations, the test personnel are fully protected against the radiations of the partitioning and of the other inner parts of the tank of the reactor.

The embodiment which has just been described is not limiting, and it is possible to imagine modifications of the embodiments of the components of this device. The centering and guide means of the measuring head can be formed differently from that which has been described and may for example be machined at the end of the horizontal body 11 of the device.

The stress and strain guages may be constructed in any form which permits accurate measurements and their translation into the form of signals.

In the same way the construction of the hydraulic circuit enabling the supply of the support jack and of the thrust jack of the measuring head may be achieved in any manner, from the moment when this circuit permits supply at fixed pressure of the support jack and supply at successive different pressures of the thrust jack of the measuring head.

Finally, the device according to the invention applies to hardness measurements on any type of nuclear reactor partitioning comprising facing vertical walls between which it is possible to introduce the horizontal body of the measuring device.

I claim:
1. Underwater measuring device, for the hardness of a vertical wall of the partitioning of the core of a pressurized water nuclear reactor comprising vertical partitions arranged in parallel and facing pairs and each assembled at a right angle with other vertical walls of the partitioning, said device comprising:
   a hollow pole for the manipulation of the device from the edge of the pool of the reactor, the pole being vertical in service position,
   a body fastened to the pole at its lower end having an axis perpendicular to the pole and hence horizontal in service position,
   a first chamber formed in the horizontal body along its axis and at one of its ends,
   a first piston mounted axially movable in the first chamber bearing a support means intended to come into contact with a first set of two walls aranged at right angles,
   a second chamber formed in the horizontal body, along its axis and at its end opposite the first chamber,
   a second piston mounted axially movable in this second chamber bearing a hardness measuring head intended to come to make an impression on one of the walls opposite the support walls, the horizontal body being intercalated between these opposite walls during the hardness measurement,
   hydraulic fluid supply means for each of the chambers of the horizontal body passing axially through the hollow vertical pole,
   measuring means for the stress exerted by the second piston on the hardness measuring head,
   accurate measuring means of the movement of the measuring head,
   and conductors passing axially through the vertical pole for the transmission of the measuring results to a measuring station arranged above the pool of the reactor.

2. Measuring device according to claim 1, wherein the horizontal body bears at its part opposite its support part, a positioning and guidance unit for the measuring head comprising supporting means for the device on the corner of the walls.

3. Measuring device according to claim 2, wherein the support means borne by the first piston and the positioning and support unit fast to the horizontal body each comprise a stop with a spherical surface for the placing of the device in supported position on one of the corner surfaces of the wall assemblies.

4. Measuring device according to claim 1, wherein the measuring means of the force exerted by the piston is intercalated between this piston and the measuring head.

5. Measuring device according to claim 2, wherein the positioning and guidance unit of the measuring head is fixed to the body in fluid-tight manner and comprises fluid-tight seals around the measuring head so as to constitute an enclosure fluid-tight to the water of the pool of the reactor containing the force and displacement measurement means.

6. Measuring device according to any of claims 1 to 5, wherein the pistons are held in retracted position inside the corresponding chambers, when these chambers are not supplied with the pressurized fluid, by helicoil return springs.

* * * * *

UNITED STATES PATENT AND TRADEMARK OFFICE
CERTIFICATE OF CORRECTION

PATENT NO. : 4,692,300
DATED : September 8, 1987
INVENTOR(S) : GERARD CRESPIN

It is certified that error appears in the above-identified patent and that said Letters Patent is hereby corrected as shown below:

The inventor's name is incorrect. The correct name is

--GERARD CRESPIN--

Signed and Sealed this

Fourteenth Day of March, 1989

Attest:

DONALD J. QUIGG

Attesting Officer

Commissioner of Patents and Trademarks